(12) United States Patent
Paterson et al.

(10) Patent No.: US 8,796,203 B2
(45) Date of Patent: *Aug. 5, 2014

(54) USE OF TIGHT JUNCTION ANTAGONISTS TO TREAT INFLAMMATORY BOWEL DISEASE

(71) Applicants: Blake Paterson, Baltimore, MD (US); Amir Tamiz, Silver Spring, MD (US); Niranjan Pandey, White Marsh, MD (US)

(72) Inventors: Blake Paterson, Baltimore, MD (US); Amir Tamiz, Silver Spring, MD (US); Niranjan Pandey, White Marsh, MD (US)

(73) Assignee: Alba Therapeutics Corporation, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/625,293

(22) Filed: Sep. 24, 2012

(65) Prior Publication Data

US 2013/0102547 A1  Apr. 25, 2013

Related U.S. Application Data

(63) Continuation of application No. 12/789,081, filed on May 27, 2010, now Pat. No. 8,299,017, which is a continuation of application No. 11/869,230, filed on Oct. 9, 2007, now abandoned.

(60) Provisional application No. 60/916,412, filed on May 7, 2007, provisional application No. 60/851,318, filed on Oct. 13, 2006, provisional application No. 60/849,802, filed on Oct. 6, 2006.

(51) Int. Cl.
*A61K 38/00* (2006.01)
*A61P 1/00* (2006.01)

(52) U.S. Cl.
USPC .......................................... 514/1.1; 514/13.2

(58) Field of Classification Search
None
See application file for complete search history.

(56) References Cited

U.S. PATENT DOCUMENTS

| | | | |
|---|---|---|---|
| 6,670,448 B2 * | 12/2003 | Fasano | 530/328 |
| 7,737,133 B2 * | 6/2010 | Devane et al. | 514/159 |
| 2005/0090473 A1 * | 4/2005 | Devane et al. | 514/150 |

* cited by examiner

*Primary Examiner* — Gyan Chandra
(74) *Attorney, Agent, or Firm* — Cooley LLP

(57) ABSTRACT

The present invention provides materials and methods for the treatment of inflammatory bowel disease (e.g., Crohn's disease and ulcerative colitis). Materials of the invention may include compositions comprising one or more tight junction antagonists and optionally one or more therapeutic agents. Methods of the invention may comprise treating a subject in need thereof with a composition comprising one or more tight junction antagonists and, optionally one or more therapeutic agents.

14 Claims, 10 Drawing Sheets

USE OF TIGHT JUNCTION ANTAGONISTS TO TREAT INFLAMMATORY BOWEL DISEASE

This Application is a continuation of application Ser. No. 12/789,081, filed May 27, 2010 (now U.S. Pat. No. 8,299,017), which is a continuation of application Ser. No. 11/869,230, filed Oct. 9, 2007 (abandoned), which claims the benefit of Provisional Application No. 60/916,412, filed May 7, 2007, Provisional Application No. 60/851,318 filed Oct. 13, 2006, and Provisional Application No. 60/849,802, filed Oct. 6, 2006.

In normal bowels, the immune reaction is regulated to maintain homeostasis of the gut. Inflammatory bowel disease (IBD) is a phrase used to describe an inappropriate immune response that occurs in the bowels of affected individuals. Two major types of IBD have been described: Crohn's disease (CD) and ulcerative colitis (UC). Both forms of IBD show abnormal profiles of T cell mediated immunity. In the gut of CD, a strong Th1 reaction is induced, while the Th2 response is upregulated in the colon of UC.

A variety of inflammatory cytokines have been implicated in IBD. For example, in UC increased proinflammatory cytokine production is observed. IL-13 was identified as an important effector cytokine in UC that impairs epithelial barrier function by affecting epithelial apoptosis, tight junctions, and restitution velocity (Heller, et al., Gastroenterology 129 (2): 550-64, 2005). TNF-α has been implicated in the pathology of CD and antibodies directed against TNF-α have been used to treat CD (see Nakamura, et al. World J Gastroenterol 2006 Aug. 7; 12(29): 4628-4635).

The barrier function of the intestines is impaired in IBD. For example, Crohn's disease is associated with increased permeability of the intestinal barrier even in quiescent patients (Oshitani, et al., Int J Mol Med 15(3):407-10, 2005). A TNF-α-induced increase in intestinal epithelial tight junction (TJ) permeability has been proposed to be an important proinflammatory mechanism contributing to intestinal inflammation in Crohn's disease and other inflammatory conditions (see Ye et al., American Journal of Physiology-Gastrointestinal and Liver Physiology, 290(3):496-504, 2006). Increased intestinal permeability during episodes of active disease correlates with destruction or rearrangement of the tight junction protein complex (Willemsen, et al. Clin. Exp. Immunol. 142(2): 275-284, 2005).

Zonula occludens toxin (ZOT), which is produced by *Vibrio cholerae*, has been characterized by Fasano et al., (*Proc. Natl. Acad. Sci., USA*, 8:5242-5246 (1991)) and the sequence has been determined (GenBank accession no. A43864). ZOT increases the intestinal permeability of rabbit ileal mucosa by modulating the structure of intercellular tight junctions.

Peptide antagonists of tight junction opening were described in U.S. Pat. No. 6,458,925, which is incorporated by reference herein in its entirety, which corresponds to WO 00/07609. Peptide antagonists of tight junction opening may bind to the receptor utilized by the zonnula occludens toxin expressed by *Vibrio cholerae*, yet not function to physiologically modulate the opening of mammalian tight junctions. The peptide antagonists competitively inhibit the binding of ZOT and zonulin to the ZOT receptor, thereby inhibiting the ability of ZOT and zonulin to physiologically modulate the opening of mammalian tight junctions.

The main treatments available for IBD are steroids and immunosuppressive agents which non-specifically reduce immunity and inflammation. These therapies are prone to undesired side effects. There remains a need in the art for treatments of IBD. This need and others are met by the present invention.

SUMMARY OF THE INVENTION

The present invention provides methods and materials for treating inflammatory bowel disease. In some embodiments, the invention provides methods of treating inflammatory bowel disease comprising administering to a subject in need thereof a composition comprising a tight junction antagonist. As used herein, a "subject" may be any mammal, for example, a human, dog, cat, horse, cow, etc. In some embodiments, a subject may be a human. In other embodiments, a subject may be a dog. Any tight junction antagonist may be used, for example, a tight junction antagonist of the invention may be a peptide. When a tight junction antagonist for use in the invention is a peptide, the peptide may comprise one or more of SEQ ID NOs: 1-24, which may be on the same or different molecules. In some embodiments, a peptide tight junction antagonist may comprise the sequence GGVLVQPG (SEQ ID NO:15). In some embodiments, the peptide tight junction antagonist may consist essentially of the sequence GGVLVQPG (SEQ ID NO:15). Compositions suitable for use in treating IBD may be formulated in any manner known to those skilled in the art. In some embodiments, a composition suitable for treating IBD may comprise a tight junction antagonist and may be a delayed release composition. Compositions for use in treating IBD, delayed release or otherwise, may comprise one or more tight junction antagonists and one or more therapeutic agents. Suitable therapeutic agents include, but are not limited to, aminosalicylates, corticosteroids, immunomodulators, antibiotics, and biologic therapeutics. In some embodiments, a composition suitable for treating IBD may comprise a peptide tight junction antagonist (e.g., a peptide comprising SEQ ID NO: 15) and a therapeutic agent, e.g., a steroid.

The present invention provides methods and materials for treating Crohn's disease. In some embodiments, the invention provides methods of treating Crohn's disease comprising administering to a subject in need thereof a composition comprising a tight junction antagonist. Any tight junction antagonist may be used, for example, a tight junction antagonist of the invention may be a peptide. When a tight junction antagonist for use in the invention is a peptide, the peptide may comprise one or more of SEQ ID NOs: 1-24, which may be on the same or different molecules. In some embodiments, a peptide tight junction antagonist may comprise the sequence GGVLVQPG (SEQ ID NO:15). In some embodiments, the peptide tight junction antagonist may consist essentially of the sequence GGVLVQPG (SEQ ID NO:15). Compositions suitable for use in treating Crohn's disease may be formulated in any manner known to those skilled in the art. In some embodiments, a composition suitable for treating Crohn's disease may comprise a tight junction antagonist and may be a delayed release composition. Compositions for use in treating Crohn's disease, delayed release or otherwise, may comprise one or more tight junction antagonists and one or more therapeutic agents. Suitable therapeutic agents include, but are not limited to, aminosalicylates, corticosteroids, immunomodulators, antibiotics, and biologic therapeutics. In some embodiments, a composition suitable for treating Crohn's disease may comprise a peptide tight junction antagonist (e.g., a peptide comprising SEQ ID NO: 15) and a therapeutic agent, e.g., a steroid.

The present invention provides methods and materials for treating ulcerative colitis. In some embodiments, the invention provides methods of treating ulcerative colitis comprising administering to a subject in need thereof a composition comprising a tight junction antagonist. Any tight junction antagonist may be used, for example, a tight junction antagonist of the invention may be a peptide. When a tight junction antagonist for use in the invention is a peptide, the peptide may comprise one or more of SEQ ID NOs: 1-24, which may be on the same or different molecules. In some embodiments, a peptide tight junction antagonist may comprise the sequence GGVLVQPG (SEQ ID NO:15). In some embodiments, the peptide tight junction antagonist may consist essentially of the sequence GGVLVQPG (SEQ ID NO:15). Compositions suitable for use in treating ulcerative colitis may be formulated in any manner known to those skilled in the art. In some embodiments, a composition suitable for treating ulcerative colitis may comprise a tight junction antagonist and may be a delayed release composition. Compositions for use in treating ulcerative colitis, delayed release or otherwise, may comprise one or more tight junction antagonists and one or more therapeutic agents. Suitable therapeutic agents include, but are not limited to, aminosalicylates, corticosteroids, immunomodulators, antibiotics, and biologic therapeutics. In some embodiments, a composition suitable for treating ulcerative colitis may comprise a peptide tight junction antagonist (e.g., a peptide comprising SEQ ID NO: 15) and a therapeutic agent, e.g., a steroid.

DETAILED DESCRIPTION OF THE INVENTION

Antagonists of tight junction opening

Figure 1:
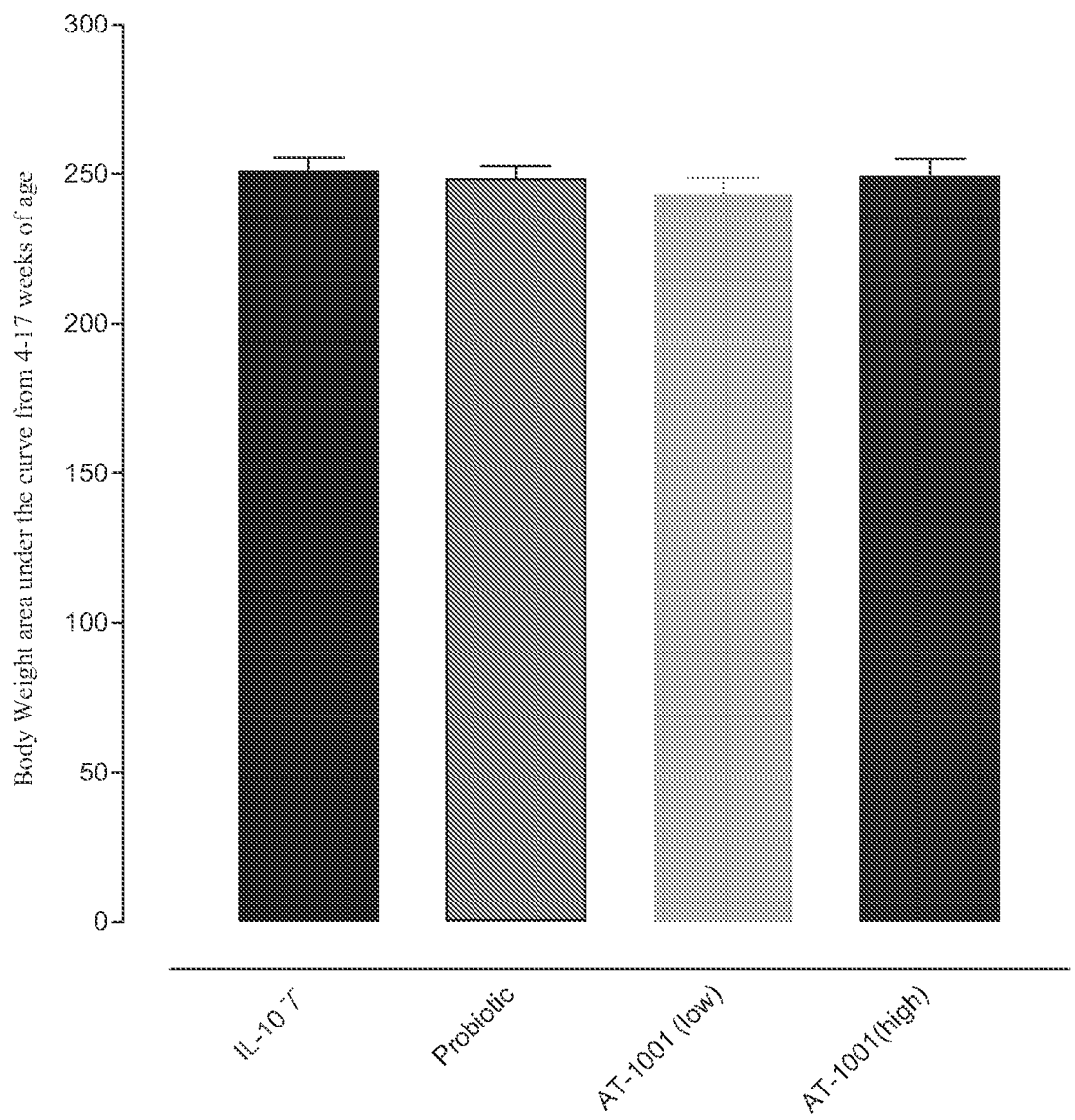
FIG. 1 shows Body Weight area under the curve from 4-17 weeks of age.

Any antagonist of tight junction opening may be used in the practice of the present invention. As used herein, tight junction antagonists prevent, inhibit or reduce the opening of tight junctions. A tight junction antagonist may bind to the zonulin receptor and prevent, inhibit, reduce or reverse the tight junction opening triggered by zonulin. For example, antagonists of the invention may comprise peptide antagonists. Examples of peptide antagonists include, but are not limited to, peptides that comprise an amino acid sequence selected from the group consisting of

```
                                         (SEQ ID NO: 1)
Gly Arg Val Cys Val Gln Pro Gly, (SEQ ID NO: 2)
Gly Arg Val Cys Val Gln Asp Gly, (SEQ ID NO: 3)
Gly Arg Val Leu Val Gln Pro Gly, (SEQ ID NO: 4)
Gly Arg Val Leu Val Gln Asp Gly, (SEQ ID NO: 5)
Gly Arg Leu Cys Val Gln Pro Gly, (SEQ ID NO: 6)
Gly Arg Leu Cys Val Gln Asp Gly, (SEQ ID NO: 7)
Gly Arg Leu Leu Val Gln Pro Gly, (SEQ ID NO: 8)
Gly Arg Leu Leu Val Gln Asp Gly, (SEQ ID NO: 9)
Gly Arg Gly Cys Val Gln Pro Gly, (SEQ ID NO: 10)
Gly Arg Gly Cys Val Gln Asp Gly, (SEQ ID NO: 11)
Gly Arg Gly Leu Val Gln Pro Gly, (SEQ ID NO: 12)
Gly Arg Gly Leu Val Gln Asp Gly, (SEQ ID NO: 13)
Gly Gly Val Cys Val Gln Pro Gly, (SEQ ID NO: 14)
Gly Gly Val Cys Val Gln Asp Gly, (SEQ ID NO: 15)
Gly Gly Val Leu Val Gln Pro Gly, (SEQ ID NO: 16)
Gly Gly Val Leu Val Gln Asp Gly, (SEQ ID NO: 17)
Gly Gly Leu Cys Val Gln Pro Gly, (SEQ ID NO: 18)
Gly Gly Leu Cys Val Gln Asp Gly, (SEQ ID NO: 19)
Gly Gly Leu Leu Val Gln Pro Gly, (SEQ ID NO: 20)
Gly Gly Leu Leu Val Gln Asp Gly, (SEQ ID NO: 21)
Gly Gly Gly Cys Val Gln Pro Gly, (SEQ ID NO: 22)
Gly Gly Gly Cys Val Gln Asp Gly, (SEQ ID NO: 23)
Gly Gly Gly Leu Val Gln Pro Gly,
and (SEQ ID NO: 24)
Gly Gly Gly Leu Val Gln Asp Gly
```

When the antagonist is a peptide, any length of peptide may be used. Generally, the size of the peptide antagonist will range from about 6 to about 100, from about 6 to about 90, from about 6 to about 80, from about 6 to about 70, from about 6 to about 60, from about 6 to about 50, from about 6 to about 40, from about 6 to about 30, from about 6 to about 25, from about 6 to about 20, from about 6 to about 15, from about 6 to about 14, from about 6 to about 13, from about 6 to about 12, from about 6 to about 11, from about 6 to about 10, from about 6 to about 9, or from about 6 to about 8 amino acids in length. Peptide antagonists of the invention may be from about 8 to about 100, from about 8 to about 90, from about 8 to about 80, from about 8 to about 70, from about 8 to about 60, from about 8 to about 50, from about 8 to about 40, from about 8 to about 30, from about 8 to about 25, from about 8 to about 20, from about 8 to about 15, from about 8 to about 14, from about 8 to about 13, from about 8 to about 12, from about 8 to about 11, or from about 8 to about 10 amino acids in length. Peptide antagonists of the invention may be from about 10 to about 100, from about 10 to about 90, from about 10 to about 80, from about 10 to about 70, from about 10 to about 60, from about 10 to about 50, from about 10 to about 40, from about 10 to about 30, from about 10 to about 25, from about 10 to about 20, from about 10 to about 15, from about 10 to about 14, from about 10 to about 13, or from about 10 to about 12 amino acids in length. Peptide antagonists of the invention may be from about 12 to about 100, from about 12 to about 90, from about 12 to about 80, from about 12 to about 70, from about 12 to about 60, from about 12 to about 50, from about 12 to about 40, from about 12 to about 30, from about 12 to about 25, from about 12 to about 20, from about 12 to about 15, or from about 12 to about 14 amino acids in length. Peptide antagonists of the invention may be from about 15 to about 100, from about 15 to about 90, from about 15 to about 80, from about 15 to about 70, from about 15 to about 60, from about 15 to about 50, from about 15 to about 40, from about 15 to about 30, from about 15 to about 25, from about 15 to about 20, from about 19 to about 15, from about 15 to about 18, or from about 17 to about 15 amino acids in length.

The peptide antagonists can be chemically synthesized and purified using well-known techniques, such as described in *High Performance Liquid Chromatography of Peptides and Proteins: Separation Analysis and Conformation,* Eds. Mant et al., C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques.

Formulations

The compositions of the invention may be formulated for enteric delivery, for example, may comprise one or more coatings, for example, delayed release coating containing one or more enteric agents. A delayed release coating is typically substantially stable in gastric fluid and substantially unstable (e.g., dissolves rapidly or is physically unstable) in intestinal fluid, thus providing for substantial release of the tight junction antagonist from the composition in the duodenum or the jejunum. Typically, compositions comprising a tight junction antagonist (e.g., peptide antagonist) comprise a pharmaceutically effective amount of the antagonist. The pharmaceutically effective amount of antagonist (e.g., peptide antagonist) employed may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation.

Compositions of the invention may comprise one or more tight junction antagonists at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 6 wt %, from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1 wt % to about 0.7 wt %, from about 0.1 wt % to about 0.6 wt %, from about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition. Compositions of the invention may comprise one or more tight junction antagonists at a level of about 0.1 wt %, about 0.2 wt %, about 0.3 wt %, about 0.4 wt %, about 0.5 wt %, about 0.6 wt %, about 0.7 wt %, about 0.8 wt %, or about 0.9 wt % based on the total weight of the composition.

Compositions of the invention may comprise one or more tight junction antagonists at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 6 wt %, from about 1 wt % to about 5 wt %, from about 1 wt % to about 4 wt %, from about 1 wt % to about 3 wt %, or from about 1 wt % to about 2 wt % of the total weight of the composition. Compositions of the invention may comprise one or more tight junction effectors at a level of about 1 wt %, about 2 wt %, about 3 wt %, about 4 wt %, about 5 wt %, about 6 wt %, about 7 wt %, about 8 wt %, or about 9 wt % based on the total weight of the composition.

The terms "stable in gastric fluid" or "stable in acidic environments" refers to a composition that releases 30% or less by weight of the total tight junction antagonist in the composition in gastric fluid with a pH of 5 or less, or simulated gastric fluid with a pH of 5 or less, in approximately sixty minutes. Compositions of the of the invention may release from about 0% to about 30%, from about 0% to about 25%, from about 0% to about 20%, from about 0% to about 15%, from about 0% to about 10%, 5% to about 30%, from about 5% to about 25%, from about 5% to about 20%, from about 5% to about 15%, from about 5% to about 10% by weight of the total tight junction antagonist in the composition in gastric fluid with a pH of 5, or less or simulated gastric fluid with a pH of 5 or less, in approximately sixty minutes. As use herein, "about" used to modify a numerical value means within 10% of the value. Compositions of the invention may release about 1%, about 2%, about 3%, about 4%, about 5%, about 6%, about 7%, about 8%, about 9%, or about 10% by weight of the total tight junction antagonist in the composition in gastric fluid with a pH of 5 or less, or simulated gastric fluid with a pH of 5 or less, in approximately sixty minutes.

The term "unstable in intestinal fluid" refers to a composition that releases 70% or more by weight of the total tight junction antagonist in the composition in intestinal fluid or simulated intestinal fluid in approximately sixty minutes. The term "unstable in near neutral to alkaline environments" refers to a composition that releases 70% or more by weight of the total amount of tight junction antagonist in the composition in intestinal fluid with a pH of 5 or greater, or simulated intestinal fluid with a pH of 5 or greater, in approximately ninety minutes. For example, a composition that is unstable in near neutral or alkaline environments may release 70% or more by weight of a tight junction antagonist peptide in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

In addition to a tight junction antagonist, compositions of the invention may further comprise one or more therapeutic agents. Therapeutic agents include, but are not limited to, steroids and other anti-inflammatory compounds. Suitable therapeutic agents may include one or more of aminosalicylates, corticosteroids, immunomodulators, antibiotics, and biologic therapies. Examples of suitable therapeutic agents that may be included in the compositions of the invention to treat IBD (e.g., Crohn's disease and/or ulcerative colitis) include, but are not limited to:

5-ASA agents (e.g., Sulfasalazine), Azulfidine®, Asacol,® Dipentum,® Pentasa,® and Rowasa®;

Antibiotics, for example, metronidazole (Flagyl®) and ciprofloxacin (Cipro®), although there are many others that may be effective in certain individuals;

Steroids, e.g., corticosteroids. Suitable steroids include, but are not limited to, prednisone, hydrocortisone, Medrol®, and budesonide multiple-release capsule MRC (EntocortREC®).

6-mercaptopurine (6-MP, Purinethol®) and azathioprine (Imuran®); and antibodies against inflammatory cytokines, e.g., Infliximab (Remicade™).

Compositions of the invention may also comprise one or more pharmaceutically acceptable excipients. Suitable excipients include, but are not limited to, buffers, buffer salts, bulking agents, salts, surface active agents, acids, bases, and binders.

Methods of Use

The compositions of the invention can be used for preventing, slowing the onset of, ameliorating and/or treating IBD (e.g., Crohn's disease and/or ulcerative colitis). In one embodiment, the present invention provides a method of treating Crohn's disease by administering a composition comprising one or more tight junction antagonists. In one embodiment, the present invention provides a method of treating ulcerative colitis by administering a composition comprising one or more tight junction antagonists.

In some embodiments, compositions of the invention may be given repeatedly over a protracted period, i.e., may be chronically administered. Typically, compositions may be administered one or more times each day in an amount suitable to prevent or reduce the likelihood of an attack of IBD (e.g., Crohn's disease and/or ulcerative colitis). Such compositions may be administered chronically, for example, one or more times daily over a plurality of days.

In some embodiments, compositions of the invention may be use to treat acute IBD (e.g., Crohn's disease and/or ulcerative colitis) attacks. Typically, embodiments of this type will require administration of the compositions of the invention to a subject undergoing an attack in an amount suitable to reduce the severity of the attack. One or more administration may be used.

EXAMPLES

Effect of AT-1001 on Intestinal Permeability and Colitis in the IL-10 KO mouse (129/Sve/IL-10KO)

The purpose of this study is to determine the ability of AT-1001, administered daily in drinking water to alter intestinal permeability (measured by absorption/excretion of lactulose and mannitol) and to inhibit the development of colitis in the 129/Svev/IL-10KO mouse.

| Group | Animal ID'S | Treatment | AT-1001 Formulation | Content (weight/ vehicle) | Anticipated* Dose, AT-1001 mg/day | Suc/lac/Man/ Sucralose Dose (0.2 ml sugar probe gavage) | # Animals per Group |
|---|---|---|---|---|---|---|---|
| 1 | 129/Svev/ IL-10KO 1M001- 1M012 | Control | — | — | 0 | Sucrose 500 mg/ml Lactulose 60 mg/ml Mannitol 40 mg/ml Sucralose 30 mg/ml | 12 |
| 2 | 129/Svev/ IL-10KO 2M001- 2M012 | Gavage of probiotic conditioned media | — | — | 0 | Sucrose 500 mg/ml Lactulose 60 mg/ml Mannitol 40 mg/ml Sucralose 30 mg/ml | 12 |
| 3 | 129/Svev/ IL-10KO 3M001- 3M012 | Low dose of AT-1001 | Neat Chemical in autoclaved, $H_2O$ | AT-1001 0.1 mg/ml $H_2O$ | 0.2 | Sucrose 500 mg/ml Lactulose 60 mg/ml Mannitol 40 mg/ml Sucralose 30 mg/ml | 12 |
| 4 | 129/Svev/ IL-10KO 4M001- 4M012 | High dose of AT-1001 | Neat Chemical in autoclaved, $H_2O$ | AT-1001 1 mg/ml $H_2O$ | 2 | Sucrose 500 mg/ml Lactulose 60 mg/ml Mannitol 40 mg/ml Sucralose 30 mg/ml | 12 |
| 5 | 129/Svev/ IL-10KO | Control for baseline zonulin level measurement | — | — | 0 | — | 4 |

*assumes 2 ml/day water consumption

Dose Administration

| | |
|---|---|
| Method and Routes | AT-1001 neat chemical in drinking water, and Suc/lac/man/sucralose given by gavage |
| Dosing | Suc/lac/man/suralose: (Groups 1-4) |
| Timepoints | 1. Weeks 1-2 Suc/lac/man/suralose solution on days 3, 6, and 9 2. Weeks 3-15 Suc/lac/man/suralose solution first day of every week |

-continued

| | Probiotic conditioned media: (Group 2) |
|---|---|
| | Daily in the mornings (Start Day 1 of study) |
| | AT-1001 Neat Chemical 0.1 mg/ml: (Group 3) |
| | Ad libidum (Start Day 1 of study) |
| | AT-1001 Neat Chemical 1 mg/ml: (Group 4) |
| | Ad libidum (Start Day 1 of study) |
| Duration | Eighty days |
| Frequency | AT-1001: continuously. Suc/lac/man/sucralose: Days 3, 6, 9, 14, 21, 28, 35, 41, 49, 56, 63, 70, 77, 84 |
| Volume | Suc/lac/man/sucralose 0.2 mL gavage per animal |

Dose Administration Details

AT-1001 neat chemical will be administered ad libitum every day starting at day 1 to Group 3 at 0.1 mg/ml and Group 4 at 1 mg/ml in sterile water via the drinking water supply. Dosing of AT-1001 will be continued when the animals are in the metabolic cages for 22 hours. Probiotic conditioned medium will be given every morning to Group 2. The solution is prepared by dissolving 0.01 g in 10 ml of MRS medium and incubating it at 37° C. for 24 h. After incubation, the tube will be centrifuged 10 minutes at 10,000 rpm. The supernatant will be filtered through a 0.22 micron filter and diluted 1:10 with MRS medium. Animals will receive 30 µl of this dilution every morning. The conditioned media must be prepared fresh every morning.

Sucrose/lactulose/mannitol/sucralose solution is prepared by dissolving Sucrose (50 mg), lactulose (6 mg), mannitol (4 mg), and sucralose (3 mg) in water (100 mL).

Each week, food and water will be removed 4 hours prior to gavage. All the collection vials will have 100 µl of paraffin oil to avoid urine evaporation and 100 µl of thymol (10% m/w in propanol). Each animal will be gavaged with 0.2 ml of sugar solution, and placed in metabolic cages with access to H$_2$O only for 22 hours. For the duration of the 22 hours, urine will be collected into previously weighed vials. At the end of the collection, the funnel of the cages will be washed off with 2 ml of water to collect any sugar that may have dried out before reaching the collection tube. After the collection of urine is complete, the animals will be placed in their respective cages, and provided with food and water. Each tube will be weighed to determine volume of urine collected. For the first 2 weeks, the animals will be handled, administered Suc/lac/man/sural-ose solution, and introduced to the cages 3 times during 10 days. After this it will be done once a week.

Test Articles

Test Articles

| | |
|---|---|
| Identification | Suc/lac/man/sucralose (Cat. # 84097, L7877, #M9647, 7106A respectively) |
| Lot/Batch Number | New sucrose has not arrived yet, 1085532, 036935, 011B99, respectively |
| Purity, Composition, and Expiry | Maintained by manufacturer |
| Storage Conditions | Room temperature |
| Source and Manufacturer | Sigma Chemical Corporation, St. Louis, MO |
| Special Handling Precautions | Appropriate PPE required (Lab coat, safety glasses, gloves). |
| Prepared | Immediately prior to dosing |
| Identification | AT1001 (neat chemical, Groups 3, and 4) |
| Lot/Batch Number | AT1001; Lot E050082 |
| Purity and Composition | >95%; neat AT1001 |
| Storage Conditions | Frozen |
| Source and Manufacturer | Solvay/Peptisyntha Inc |
| Special Handling Precautions | Appropriate PPE required (Lab coat, safety glasses, and gloves) |
| Prepared | Freshly prepared each day prior to dosing |
| Identification | Probiotic conditioned media |
| Lot/Batch Number | 5160D5 |
| Storage conditions | Room temperature |
| Source and manufacturer | Sigma-Tau Pharmaceuticals |
| Special Handling Precautions | Use aseptic technique and appropriate PPE required (Lab coat, safety glasses, gloves). |
| Prepared | Dissolve 0.1 g in 10 ml of MRS media, incubate at 37 C. for 24 hours. Filter through 0.22 µm membrane and dilute filtrate 1/10 in MRS media. Gavage animals with 30 µl. |

Preparation of Test Articles

| Test Article | Suc/lac/man/suralose solution (Groups 1, 2, 3, and 4) | AT1001 (neat chemical) (Group 3) | AT1001 (neat chemical) (Group 4) |
|---|---|---|---|
| Type of Formulation | Solution in water | Oral solution in drinking water | Oral solution in drinking water |
| Method of Preparation | Weigh 50 g of sucrose, 6 g of lactulose, 4 g of mannitol and 3 g of sucralose and dissolve in 100 ml of sterile water. | Weigh 10 mg of neat AT1001. Dissolve in 100 mL sterile water. | Weigh 100 mg of neat AT1001. Dissolve in 100 mL sterile water. |
| Frequency of Preparation | Every week | Every day | Every day |
| Dose Concentration | Sucrose 500 mg/ml Lactulose 60 mg/ml Mannitol 40 mg/ml Sucralose 30 mg/ml | 0.1 mg/ml | 1 mg/ml |
| Dose Volume | 0.2 ml | N/A | N/A |
| Storage Conditions | Refrigerated | Refrigerated | Refrigerated |

Test System

| | |
|---|---|
| Species/Strain or Breed | 129/Svev/IL-10 KO mouse |
| Age at Study Initiation | Approximately 28 days |
| Weight | Approximately 10 grams at study initiation and 20 grams at study termination |
| Acclimation | At least 3 days |
| Selection Criteria/ Randomization | Randomized assignment of group and animal number prior to study start |
| Identification | Ear markings and cage cards |
| Animal Use Protocol Number | 138 |

Animals to be used on this study will be selected on the basis of acceptable findings from physical examination and body weights. The animals will then be assigned to treatment groups prior to dosing.

Environmental Conditions

| | |
|---|---|
| Caging | Individually housed cages and in metabolism cages during urine collection |
| Bedding | Direct bedding - wood chips prior to study start |
| Temperature | Approximate range 72 +/− 4° F. |
| Humidity | Range 30% to 70% |
| Lighting | Approximate 12-hour light, 12-hour dark cycle. The lighting cycle may be interrupted for performance of protocol-defined activities. |
| Water | Sterile filtered (0.22 micron filter) water |
| Diet | Certified Purina Rodent Meal 5001. |

Clinical and Physical Examinations

| | |
|---|---|
| Survival and Moribundity Observations | Throughout treatment periods of study |
| Clinical Signs | Once daily |
| Unscheduled Observations | To be performed at the discretion of the study director/principal investigator |
| Physical Examinations | To be conducted once prior to the initiation of dosing |
| Routine Body Weights | Prior to randomization and the first day of every week thereafter |
| Food Consumption | Two times a week. Mice will be fasted 4 hours prior to each sugar gavage |
| Water Consumption | Every day. |
| Stool Collection | First day of every week and screened for the presence of blood |

Clinical Pathology
Urine Collection

During each intestinal permeability trial, all subjects will be gavaged with suc/lac/man/sucralose solution and placed in metabolic cages immediately after to enable urine collection. Urine from each animal will be collected for 22 hours in chilled collection tubes, treated with 100 μL of a 10% Thymol solution (1.0 g/10 mL isopropanol) and paraffin oil (100 μL, to prevent urine evaporation) from the following interval post dosing 24 hours. Samples will be frozen at −80° C. until analysis. All sugars will be quantified by ion exchange HPLC. LAMA ratio, total sucrose and total sucralose will be obtained per measurement.

Stool Sample Collection

On the first day of every week stool sample will be collected from every animal and screened for the presence of blood. Stool samples will also be collected at the termination of the study.

Sample Storage Conditions 50-100 μl serum from animals in Group 5 will be frozen until zonulin measurements made. 100 μl serum from animals from Groups 1-4 at Day 57 and at day 77 will be frozen at −20° C. until zonulin measurements made.

Sacrifice Schedule

Animals found dead will be refrigerated and necropsied at the earliest possible time (within working hours). Terminal body weight organ weights will not be taken from animals found dead. Protocol defined tissues will be collected.

Moribund/unscheduled animals that are sacrificed during normal working hours will be taken immediately to necropsy. A terminal body weight will be taken and the animal will be necropsied. Protocol defined tissues for histology will be taken. Moribund/unscheduled sacrifice animals that are sacrificed outside of normal working hours will be refrigerated after a terminal body weight and necropsied at the earliest possible time (within working hours). Organ weights will not be collected unless the entire study is sacrificed early and control organ weights can be collected at the same time or the study is taken down at the scheduled sacrifice.

| | |
|---|---|
| Animals Found Dead | Animals found dead will be refrigerated and necropsied at the earliest possible time (within working hours). Gross findings will be noted. |
| Moribund/ Unscheduled Sacrifice | Moribund/unscheduled sacrifice animals that are sacrificed outside of normal working hours will be refrigerated and necropsied at the earliest possible time (within working hours). Gross findings will be noted. Protocol-defined tissues will be collected. |
| Sacrifice Schedule | 1. At time 0, all 4 animals of group 5 will be sacrificed. 50-100 μl serum will also be collected to measure zonulin levels.<br>2. After 8 weeks, on day 57, 4 animals from the Groups 1-4 will be sacrificed and their intestinal permeability (small bowel and colon) will be measured using Ussing chambers and samples from both sites will be assessed for histology, MPO and cytokine secretion. 100 μl of serum will be collected from these animals and sent to Alba Therapeutics for zonulin levels determination.<br>3. On day 77, after final urine collection, all animals will be sacrificed for measurements as above. |
| Number of Animals (survival permitting) | All |
| Method of Euthanasia | Cervical dislocation |
| Fasting Requirements | Animals will be fasted overnight prior to necropsy |
| Terminal Body Weight | Will be taken at necropsy |
| Macroscopic Examination | Will be performed by the study pathologist at necropsy |

Immediately upon expiration, stomachs, small intestines, and colons will be collected and weighed. Each tissue will be scored for macroscopic lesions to assess intestinal damage by the Study Pathologist. ELISAs will be performed on each tissue to measure the levels of MPO, IL-8, TNFα, and IFNγ. A section of the tissues will be fixed in formalin for HE histology. The day after the final intestinal permeability measures on day 77, all surviving animals will be euthanized and intestinal tissues collected and processed.

Clinical observations, physical examinations, and body weights will be recorded on appropriate paper forms. Sucrose, lactulose, mannitol, and sucralose and lactulose:mannitol ratios will be determined according to the published procedures.

Data Acquisition

The following data will be acquired

| Data Type | Schedule |
|---|---|
| Weights | 1. Weigh all animals on the first day of every week<br>2. Weigh all animals at sacrifice<br>3. Week 8<br>   Sacrifice 4 animals from each group to dissect out stomachs, small intestines, and colons and weigh them |

| Data Type | Schedule | |
|---|---|---|
| | 4. | Week 11<br>Sacrifice the remaining 8 animals from each group to dissect out stomachs, and intestines, and colons and weigh them |
| Suc/lac/manLAMA in urine | 1. | Weeks 1-2<br>Administer Suc/lac/man/suralose and collect urine for 22 hours on days 3, 6, 9 |
| | 2. | Weeks 3-11<br>Administer Suc/lac/man/suralose and collect urine urine for 22 hours on days 14, 21, 28, 35, 41, 49, 56, 63, 70, 77 |
| Intestinal permeability with Ussing chambers | 1. | Week 8 - Day 57 of study<br>Sacrifice 4 animals from each group to dissect out stomachs, small intestines and colons and measure intestinal permeability |
| | 2. | Week 11 - termination of study at day 77<br>Sacrifice the remaining 8 animals from each group to dissect out stomachs, small intestines and colons and measure intestinal permeability |
| Scoring lesions histologically | 1. | Day 1<br>Dissect out stomachs, small intestines and colons of 4 animals in Group 5 for scoring macroscopic lesions as control, fix sections for histology. |
| | 2. | Week 8 - Day 57 of study<br>Dissect out stomachs, small intestines and colons of 4 animals from Groups 1-4 for scoring macroscopic lesions, fix sections for histology |
| | 3. | Week 11- Day 77 of study<br>Dissect out stomachs, small intestines and colons of remaining 8 animals from Groups 1-4 for scoring macroscopic lesions, fix sections for histology |
| Zonulin levels | 1. | Sacrifice all 4 animals from Group 5 to measure zonulin levels day 1 |
| | 2. | Week 8 - Day 57 of study<br>Measure zonulin levels in the animals from Groups 1-4 sacrificed on this day |
| | 2. | Week 11- Day 77 of study<br>Measure zonulin levels in the animals from Groups 1-4 sacrificed on this day |
| Levels of MPO, IL-8, TNF-α, IFNγ | 1. | Measure levels of these proteins in animals from Group 5 |
| | 2. | Measure levels of these proteins in animals from Groups 1-4 at the beginning of Week 8 - Day 57 of study |
| | 3. | Measure levels of these proteins in animals from Groups 1-4 when study is terminated at Week 11- Day 77 of study |
| Water consumption | 1. | Measure water consumption daily for dose measurement |

Figure 2:
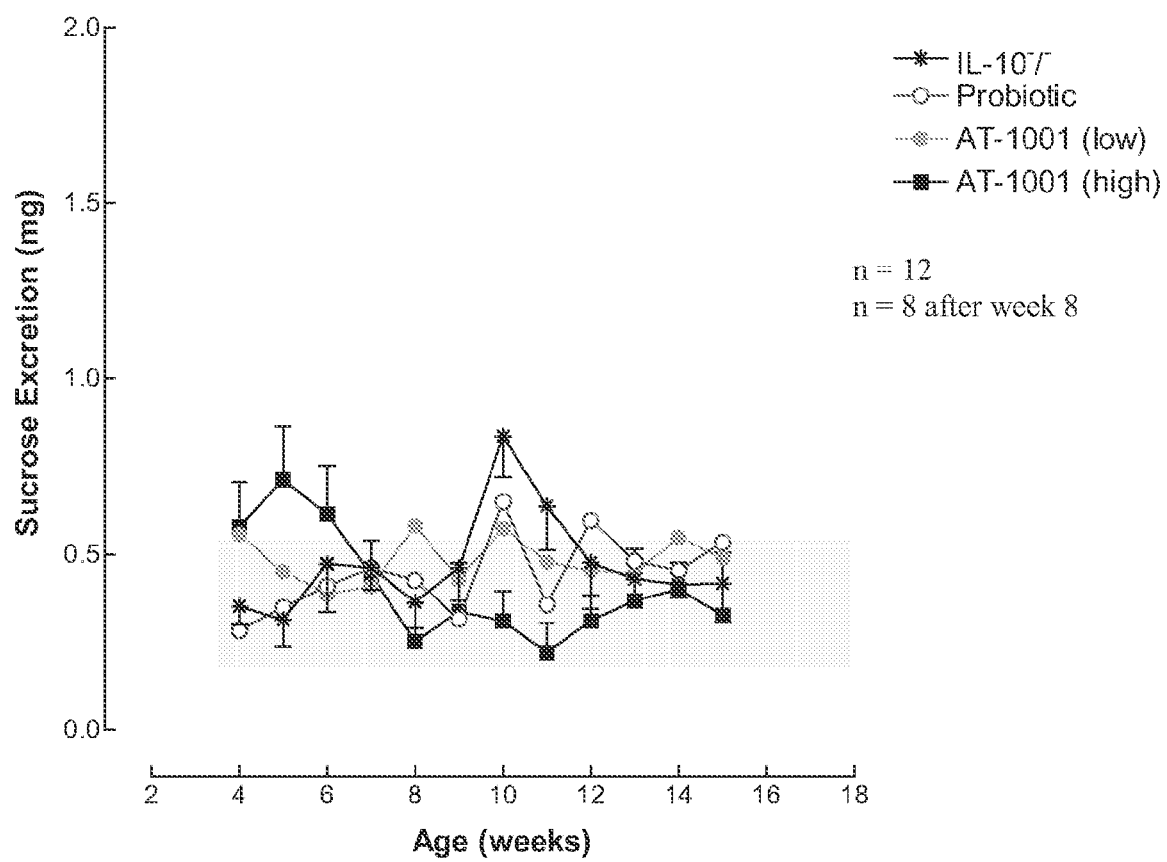
FIG. 2 shows a measurement of Gastric Permeability measured as sucrose excretion.
Figure 3:
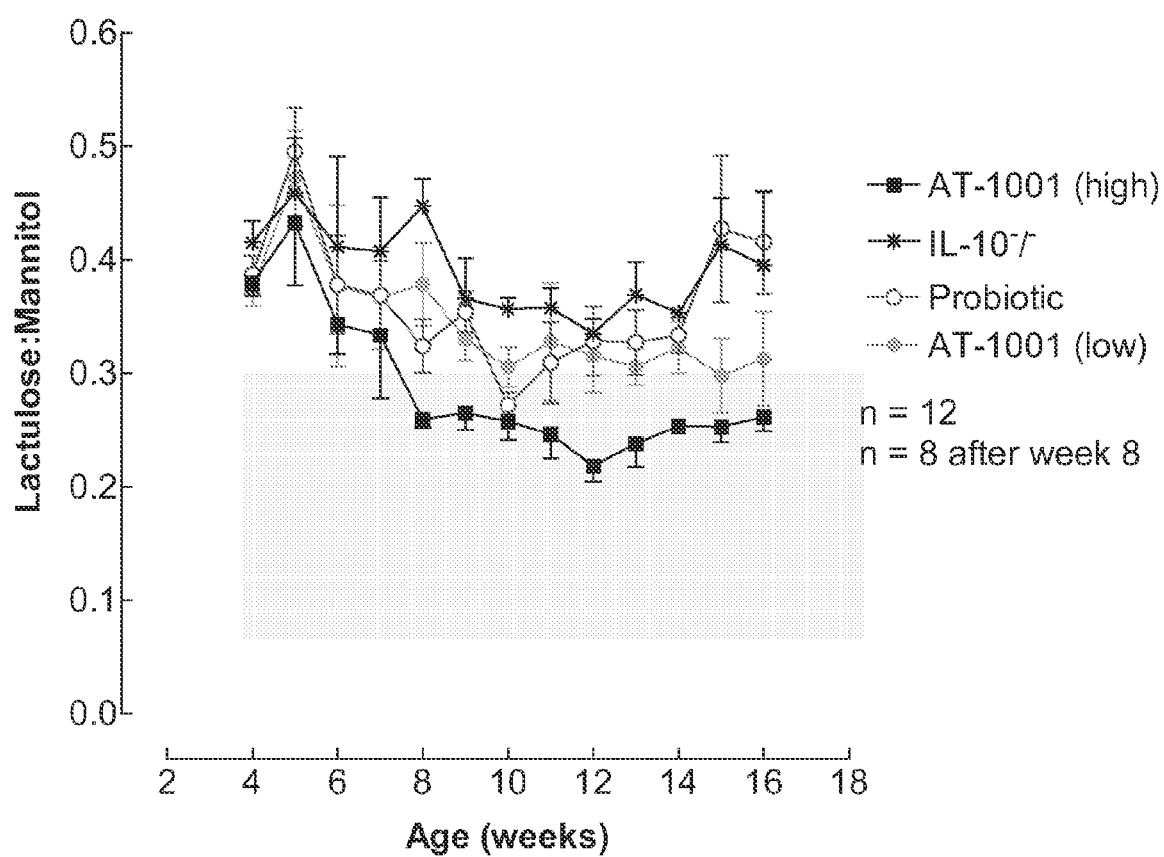
FIG. 3 shows Small Intestinal Permeability measured by lactulose mannitol test.
Figure 4:
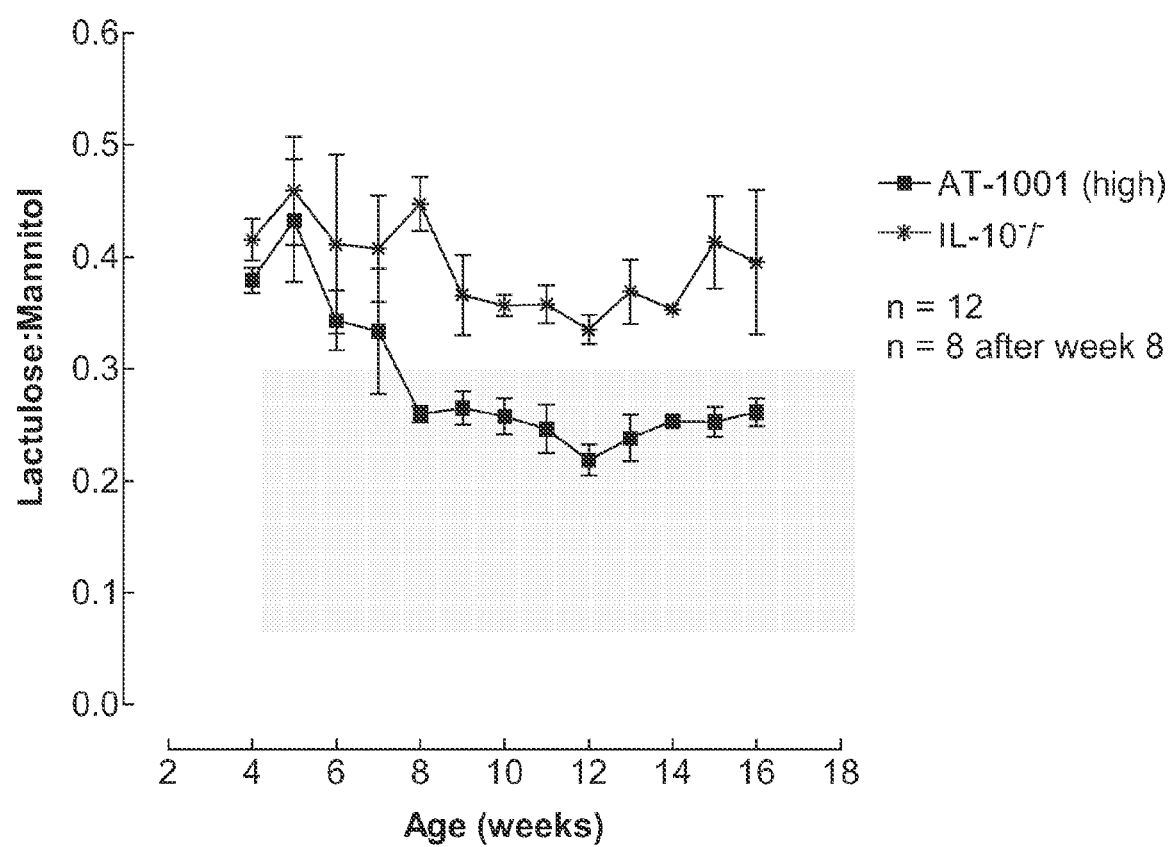
FIG. 4 shows Small Intestinal Permeability measured by lactulose mannitol test.

FIGS. 1-4 show that development of disease is associated with an increase in small intestinal permeability. This increase can be abrogated by high dose AT-1001.

Figure 5:
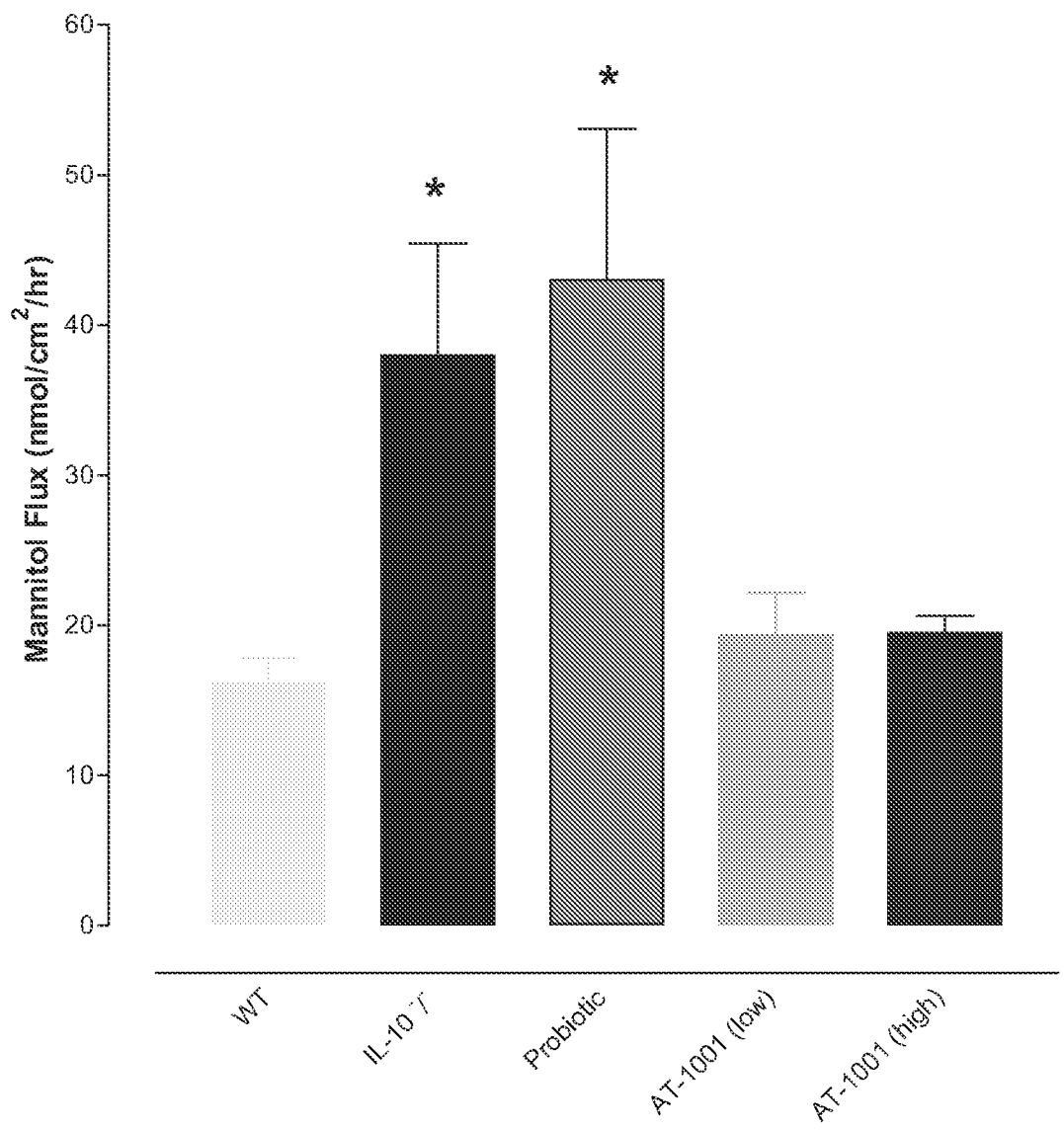
FIG. 5 shows in vitro measurement of colonic permeability at 8 weeks of age.
Figure 6:
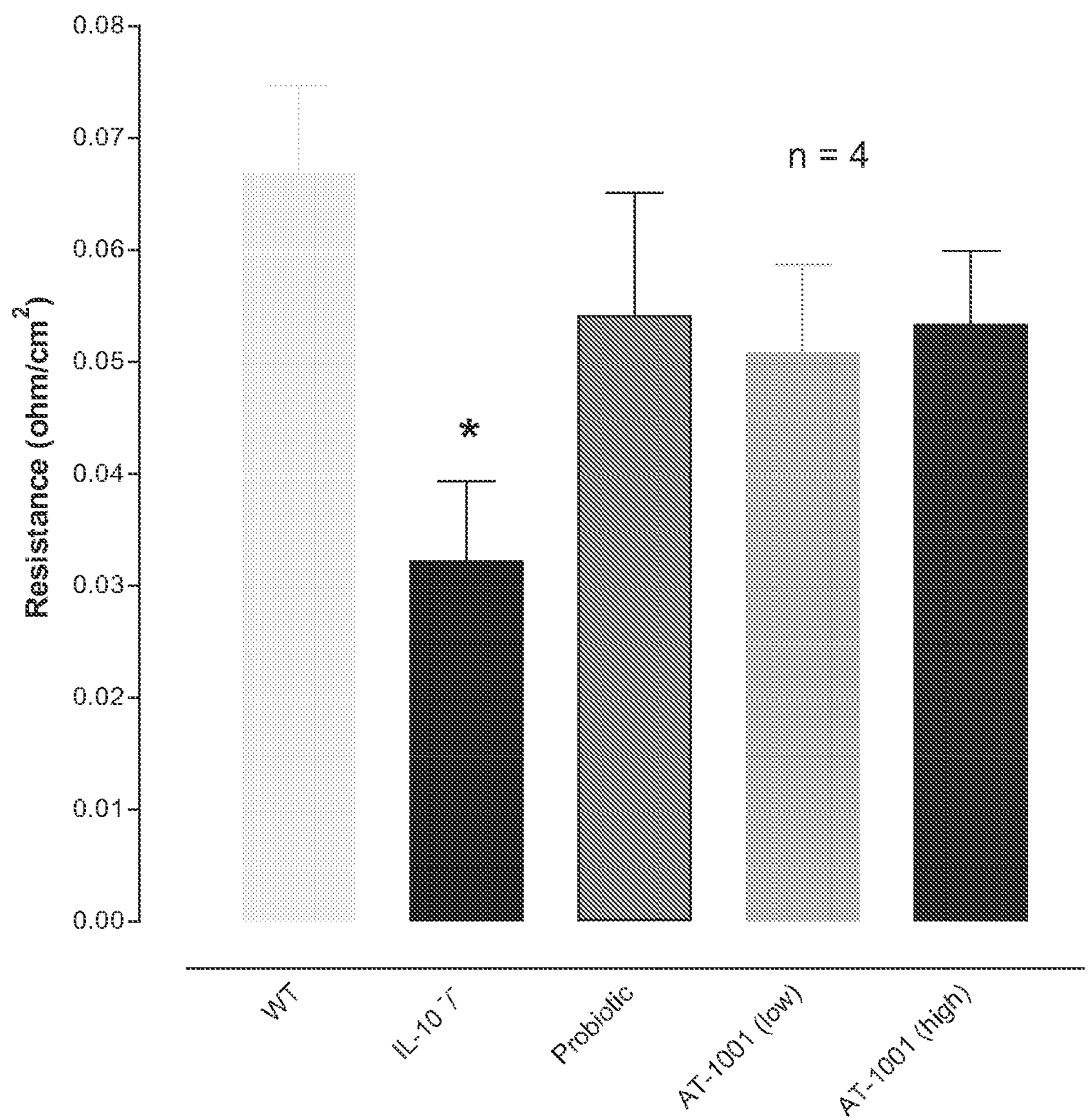
FIG. 6 shows in vitro colonic electrical resistance at 8 weeks of age.
Figure 7:
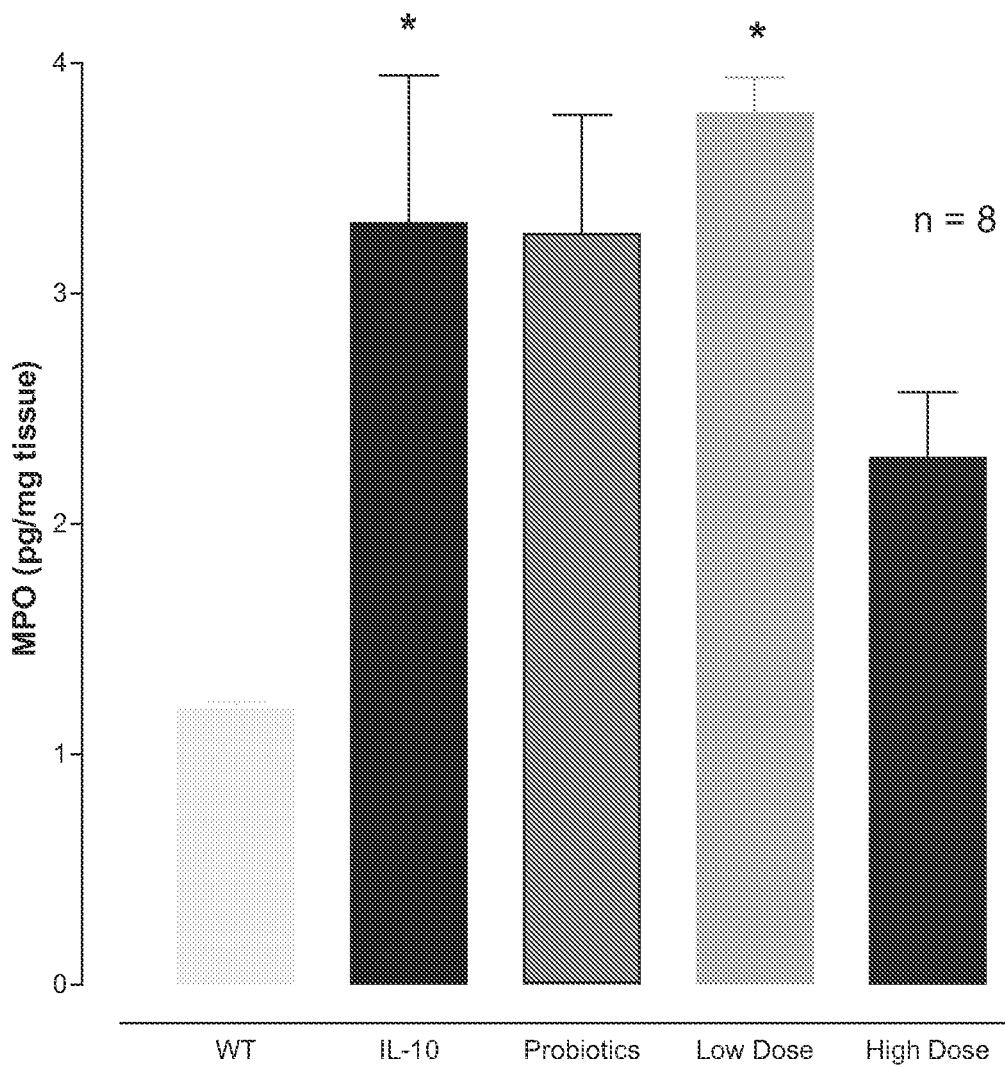
FIG. 7 shows colonic inflammation (neutrophil infiltration) at 17 weeks.
Figure 8:
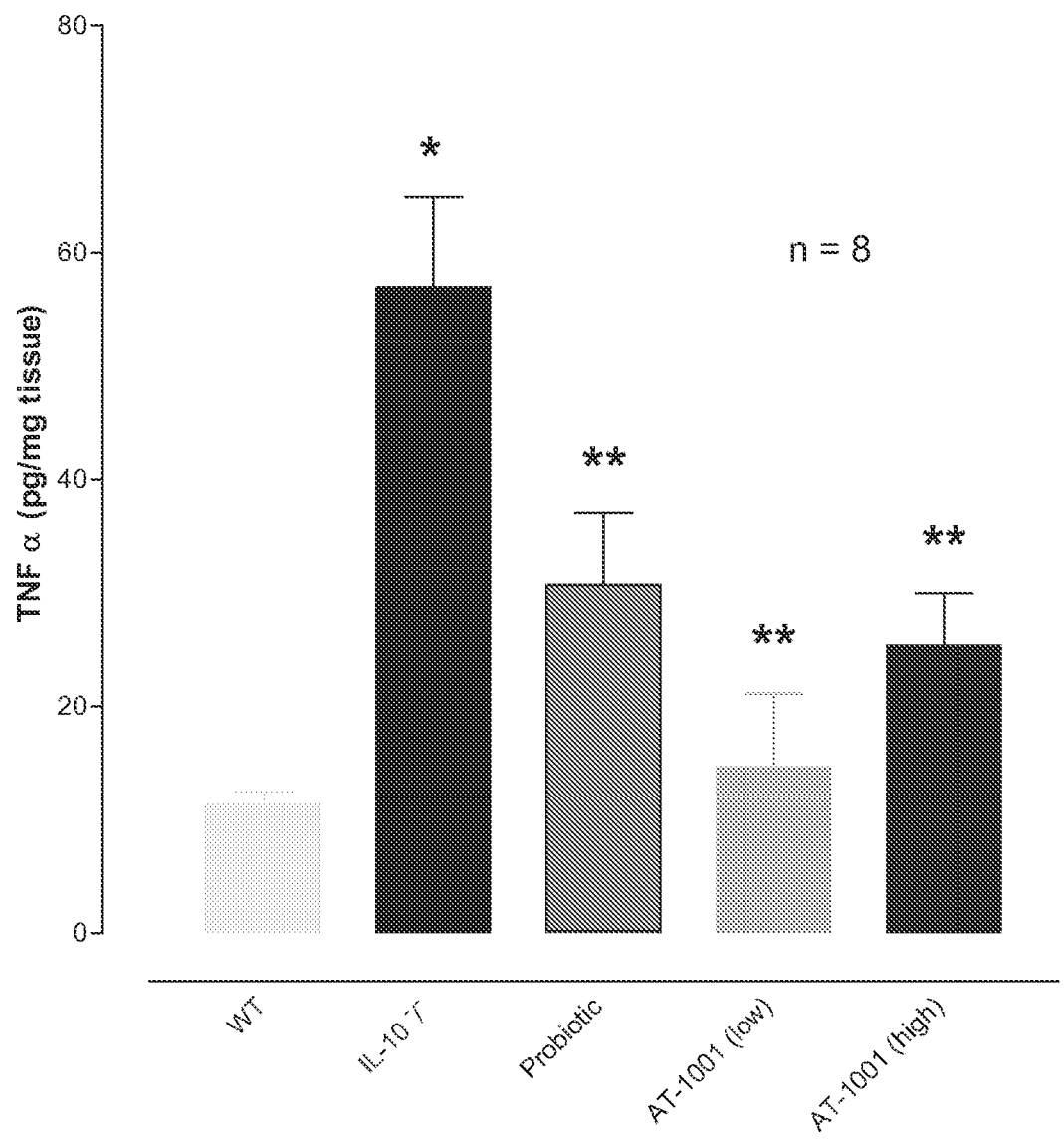
FIG. 8 shows colonic inflammation at 17 weeks (TNF secretion over 24 hours).
Figure 9:
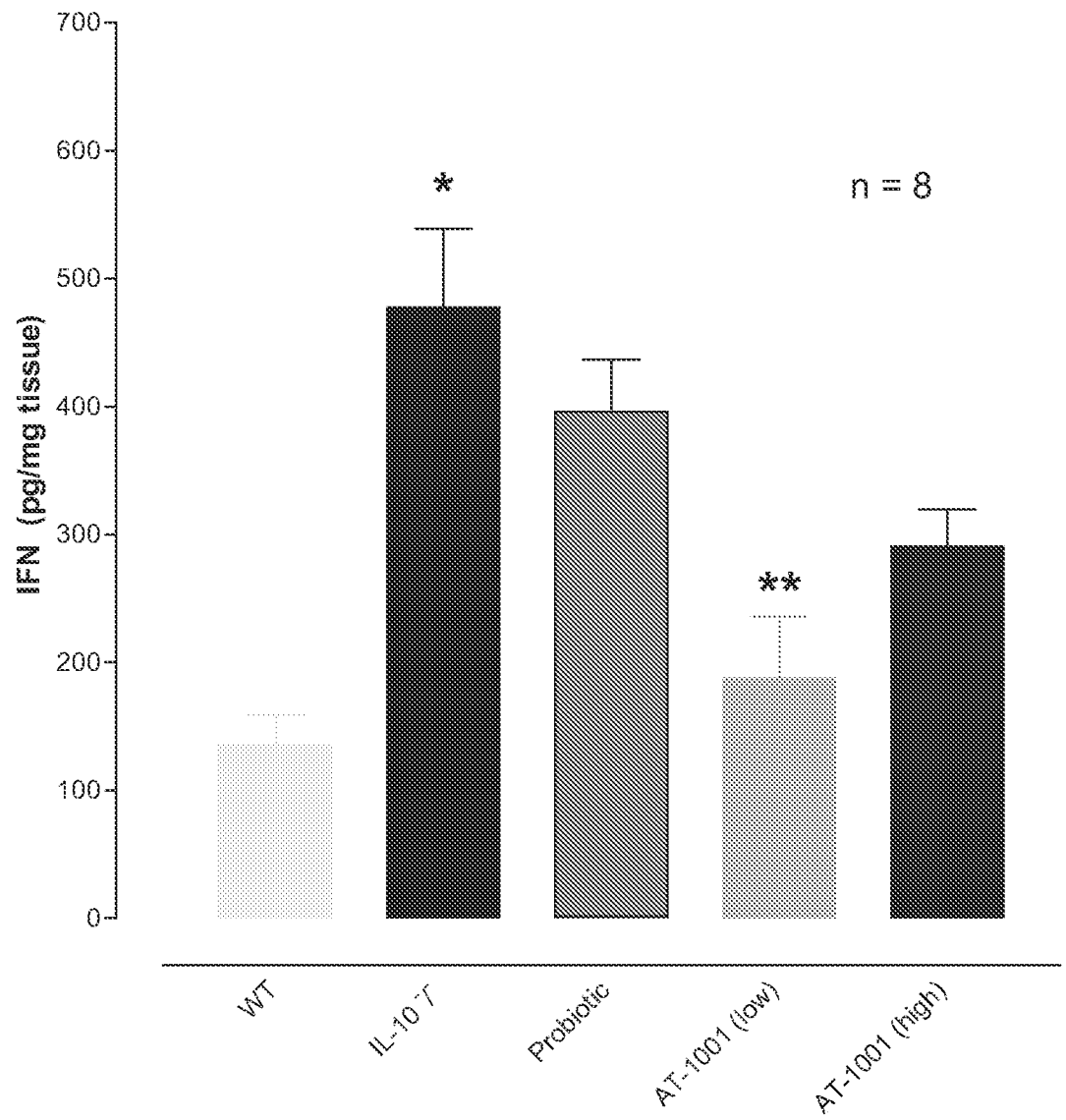
FIG. 9 shows colonic inflammation at 17 weeks (IFN secretion over 24 hours).
Figure 10:
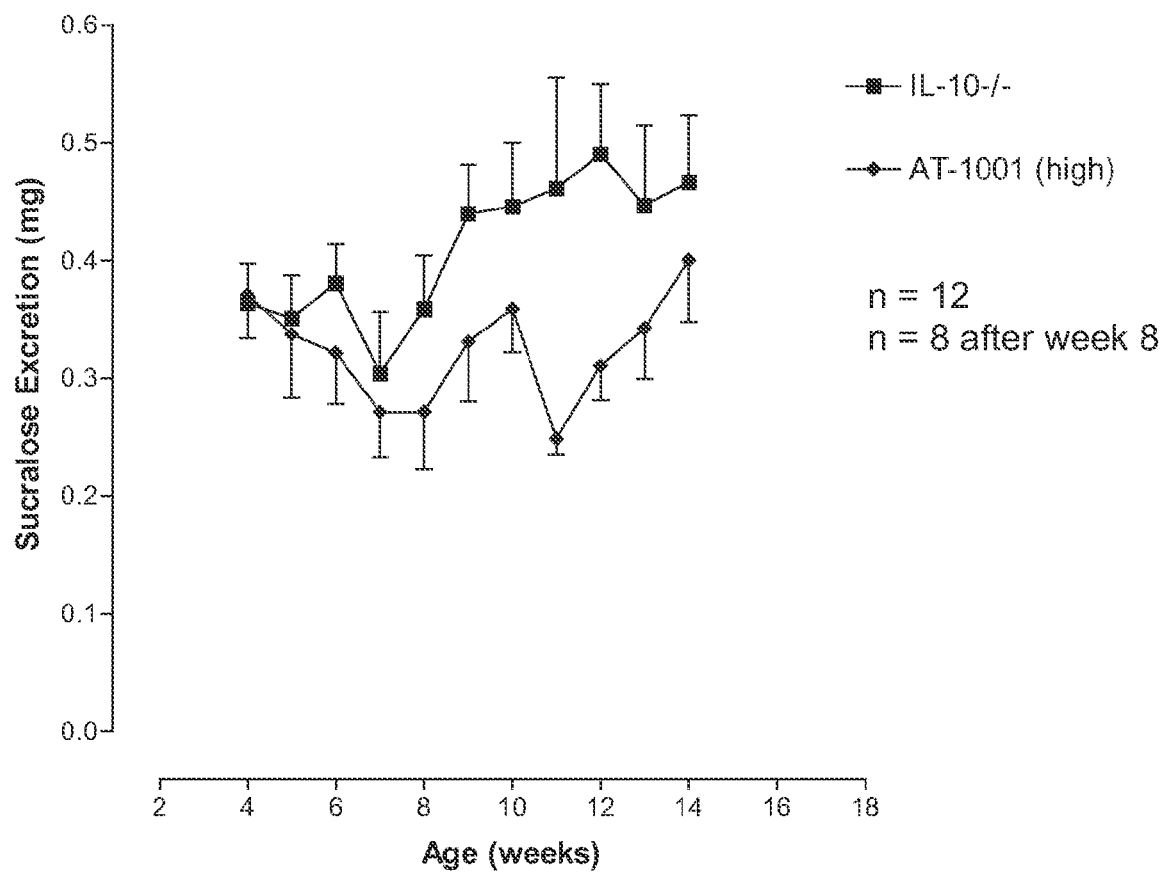
FIG. 10 shows Colonic Permeability as measured by sucralose excretion.

FIG. 5-10 show the results of analysis of disease in the colon. Disease in the colon was evaluated at both 8 and 17 week time points. The former with Ussing chamber measurements and the latter with histology, mucosal cytokine secretion, MPO and sucralose permeability. At 8 weeks of age AT-1001 reduced colonic permeability to mannitol and prevented the reduction in electrical resistance observed in the untreated animals. At 17 weeks AT-1001 reduced all tissue markers of colonic inflammation that were measured All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for treating Inflammatory Bowel Disease (IBD) in a patient, the method comprising:
    administering a peptide having the amino acid sequence GGVLVQPG (SEQ ID NO:15) to the colon of a patient having IBD.

2. The method of claim 1, wherein the peptide is administered in a delayed release composition that is stable in gastric fluid.

3. The method of claim 1, wherein the patient has Crohn's Disease.

4. The method of claim 1, wherein the patient has ulcerative colitis.

5. The method of claim 1, wherein the peptide is further administered to the small intestine of the patient.

6. The method of claim 1, further comprising, administering an active agent selected from an aminosalicylate, corticosteroid, immunomodulator, or antibiotic.

7. The method of claim 6, wherein the aminosalicylate is 5-aminosalicylic acid (5-ASA).

8. The method of claim 1, wherein the peptide is administered one or more times per day for a plurality of days.

9. The method of claim 8, wherein the peptide is administered chronically.

10. The method of claim 1, wherein the patient is not undergoing an acute Inflammatory Bowel Disease (IBD) attack at the time the peptide is administered.

11. The method of claim 1, wherein the patient is undergoing an acute attack of Inflammatory Bowel Disease (IBD) at the time the peptide is administered.

12. The method of claim 1, wherein the patient is a human.

13. The method of claim 1, wherein the patient is a dog.

14. A method for treating chronic Inflammatory Bowel Disease (IBD) in a patient in need thereof, the method comprising: administering to the patient one or more times per day for a plurality of days, a peptide having the amino acid sequence GGVLVQPG (SEQ ID NO:15), the peptide being administered in a delayed release composition to the colon of the subject.

* * * * *

SEQUENCE LISTING

<160> NUMBER OF SEQ ID NOS: 24

<210> SEQ ID NO 1
<211> LENGTH: 8
<212> TYPE: PRT
<213> ORGANISM: Artificial Sequence
<220> FEATURE:
<223> OTHER INFORMATION: chemically synthesized

<400> SEQUENCE: 1

Gly Arg Val Cys Val Gln Pro Gly
1               5

-continued

```
<210> SEQ ID NO 2
<211> LENGTH: 8
<212> TYPE: PRT
<213> ORGANISM: Artificial Sequence
<220> FEATURE:
<223> OTHER INFORMATION: chemically synthesized

<400> SEQUENCE: 2

Gly Arg Val Cys Val Gln Asp Gly
1               5

<210> SEQ ID NO 3
<211> LENGTH: 8
<212> TYPE: PRT
<213> ORGANISM: Artificial Sequence
<220> FEATURE:
<223> OTHER INFORMATION: chemically synthesized

<400> SEQUENCE: 3

Gly Arg Val Leu Val Gln Pro Gly
1               5

<210> SEQ ID NO 4
<211> LENGTH: 8
<212> TYPE: PRT
<213> ORGANISM: Artificial Sequence
<220> FEATURE:
<223> OTHER INFORMATION: chemically synthesized

<400> SEQUENCE: 4

Gly Arg Val Leu Val Gln Asp Gly
1               5

<210> SEQ ID NO 5
<211> LENGTH: 8
<212> TYPE: PRT
<213> ORGANISM: Artificial Sequence
<220> FEATURE:
<223> OTHER INFORMATION: chemically synthesized

<400> SEQUENCE: 5

Gly Arg Leu Cys Val Gln Pro Gly
1               5

<210> SEQ ID NO 6
<211> LENGTH: 8
<212> TYPE: PRT
<213> ORGANISM: Artificial Sequence
<220> FEATURE:
<223> OTHER INFORMATION: chemically synthesized

<400> SEQUENCE: 6

Gly Arg Leu Cys Val Gln Asp Gly
1               5

<210> SEQ ID NO 7
<211> LENGTH: 8
<212> TYPE: PRT
<213> ORGANISM: Artificial Sequence
<220> FEATURE:
<223> OTHER INFORMATION: chemically synthesized

<400> SEQUENCE: 7

Gly Arg Leu Leu Val Gln Pro Gly
1               5
```

```
<210> SEQ ID NO 8
<211> LENGTH: 8
<212> TYPE: PRT
<213> ORGANISM: Artificial Sequence
<220> FEATURE:
<223> OTHER INFORMATION: chemically synthesized

<400> SEQUENCE: 8

Gly Arg Leu Leu Val Gln Asp Gly
1               5

<210> SEQ ID NO 9
<211> LENGTH: 8
<212> TYPE: PRT
<213> ORGANISM: Artificial Sequence
<220> FEATURE:
<223> OTHER INFORMATION: chemically synthesized

<400> SEQUENCE: 9

Gly Arg Gly Cys Val Gln Pro Gly
1               5

<210> SEQ ID NO 10
<211> LENGTH: 8
<212> TYPE: PRT
<213> ORGANISM: Artificial Sequence
<220> FEATURE:
<223> OTHER INFORMATION: chemically synthesized

<400> SEQUENCE: 10

Gly Arg Gly Cys Val Gln Asp Gly
1               5

<210> SEQ ID NO 11
<211> LENGTH: 8
<212> TYPE: PRT
<213> ORGANISM: Artificial Sequence
<220> FEATURE:
<223> OTHER INFORMATION: chemically synthesized

<400> SEQUENCE: 11

Gly Arg Gly Leu Val Gln Pro Gly
1               5

<210> SEQ ID NO 12
<211> LENGTH: 8
<212> TYPE: PRT
<213> ORGANISM: Artificial Sequence
<220> FEATURE:
<223> OTHER INFORMATION: chemically synthesized

<400> SEQUENCE: 12

Gly Arg Gly Leu Val Gln Asp Gly
1               5

<210> SEQ ID NO 13
<211> LENGTH: 8
<212> TYPE: PRT
<213> ORGANISM: Artificial Sequence
<220> FEATURE:
<223> OTHER INFORMATION: chemically synthesized

<400> SEQUENCE: 13

Gly Gly Val Cys Val Gln Pro Gly
1               5
```

-continued

```
<210> SEQ ID NO 14
<211> LENGTH: 8
<212> TYPE: PRT
<213> ORGANISM: Artificial Sequence
<220> FEATURE:
<223> OTHER INFORMATION: chemically synthesized

<400> SEQUENCE: 14

Gly Gly Val Cys Val Gln Asp Gly
1               5

<210> SEQ ID NO 15
<211> LENGTH: 8
<212> TYPE: PRT
<213> ORGANISM: Artificial Sequence
<220> FEATURE:
<223> OTHER INFORMATION: chemically synthesized

<400> SEQUENCE: 15

Gly Gly Val Leu Val Gln Pro Gly
1               5

<210> SEQ ID NO 16
<211> LENGTH: 8
<212> TYPE: PRT
<213> ORGANISM: Artificial Sequence
<220> FEATURE:
<223> OTHER INFORMATION: chemically synthesized

<400> SEQUENCE: 16

Gly Gly Val Leu Val Gln Asp Gly
1               5

<210> SEQ ID NO 17
<211> LENGTH: 8
<212> TYPE: PRT
<213> ORGANISM: Artificial Sequence
<220> FEATURE:
<223> OTHER INFORMATION: chemically synthesized

<400> SEQUENCE: 17

Gly Gly Leu Cys Val Gln Pro Gly
1               5

<210> SEQ ID NO 18
<211> LENGTH: 8
<212> TYPE: PRT
<213> ORGANISM: Artificial Sequence
<220> FEATURE:
<223> OTHER INFORMATION: chemically synthesized

<400> SEQUENCE: 18

Gly Gly Leu Cys Val Gln Asp Gly
1               5

<210> SEQ ID NO 19
<211> LENGTH: 8
<212> TYPE: PRT
<213> ORGANISM: Artificial Sequence
<220> FEATURE:
<223> OTHER INFORMATION: chemically synthesized

<400> SEQUENCE: 19

Gly Gly Leu Leu Val Gln Pro Gly
1               5
```

```
<210> SEQ ID NO 20
<211> LENGTH: 8
<212> TYPE: PRT
<213> ORGANISM: Artificial Sequence
<220> FEATURE:
<223> OTHER INFORMATION: chemically synthesized

<400> SEQUENCE: 20

Gly Gly Leu Leu Val Gln Asp Gly
1               5

<210> SEQ ID NO 21
<211> LENGTH: 8
<212> TYPE: PRT
<213> ORGANISM: Artificial Sequence
<220> FEATURE:
<223> OTHER INFORMATION: chemically synthesized

<400> SEQUENCE: 21

Gly Gly Gly Cys Val Gln Pro Gly
1               5

<210> SEQ ID NO 22
<211> LENGTH: 8
<212> TYPE: PRT
<213> ORGANISM: Artificial Sequence
<220> FEATURE:
<223> OTHER INFORMATION: chemically synthesized

<400> SEQUENCE: 22

Gly Gly Gly Cys Val Gln Asp Gly
1               5

<210> SEQ ID NO 23
<211> LENGTH: 8
<212> TYPE: PRT
<213> ORGANISM: Artificial Sequence
<220> FEATURE:
<223> OTHER INFORMATION: chemically synthesized

<400> SEQUENCE: 23

Gly Gly Gly Leu Val Gln Pro Gly
1               5

<210> SEQ ID NO 24
<211> LENGTH: 8
<212> TYPE: PRT
<213> ORGANISM: Artificial Sequence
<220> FEATURE:
<223> OTHER INFORMATION: chemically synthesized

<400> SEQUENCE: 24

Gly Gly Gly Leu Val Gln Asp Gly
1               5
```